United States Patent [19]

Ramsey

[11] Patent Number: 5,667,519
[45] Date of Patent: Sep. 16, 1997

[54] KNIFE FOR LAPAROSCOPIC SURGERY

[75] Inventor: Don E. Ramsey, Springfield, Ill.

[73] Assignee: Ramsey Instruments Partnership, LLP, Columbia, Md.

[21] Appl. No.: 640,614

[22] Filed: May 2, 1996

[51] Int. Cl.⁶ .................................................. A61B 17/32
[52] U.S. Cl. .................................... 606/167; 606/170
[58] Field of Search .......................... 606/167, 169, 606/170, 171, 172, 159

[56] References Cited

U.S. PATENT DOCUMENTS

| | | | |
|---|---|---|---|
| 5,263,937 | 11/1993 | Shipp | 604/164 |
| 5,273,024 | 12/1993 | Menon et al. | 128/4 |
| 5,372,588 | 12/1994 | Farley et al. | 606/167 |
| 5,569,292 | 10/1996 | Scwemberger et al. | 606/167 |

FOREIGN PATENT DOCUMENTS 1181640A  9/1985  U.S.S.R. ................................ 606/167

*Primary Examiner*—Michael Buiz
*Assistant Examiner*—Kevin Truong
*Attorney, Agent, or Firm*—William S. Ramsey

[57] ABSTRACT

This incision knife is used to enlarge the incision made in a laparoscopic cholecystectomy. This enlargement allows the passage of an intact gallbladder through the incision, thereby reducing the probability of gallbladder rupture. The incision knife makes a controlled cut and has a ward which protects the gall bladder from injury by the blade.

6 Claims, 3 Drawing Sheets

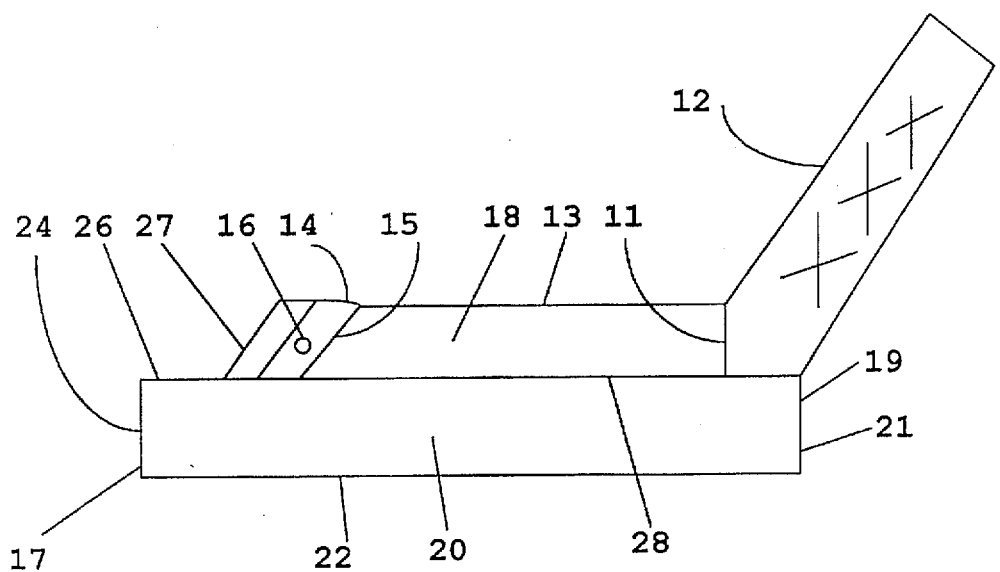
FIG. 1    10
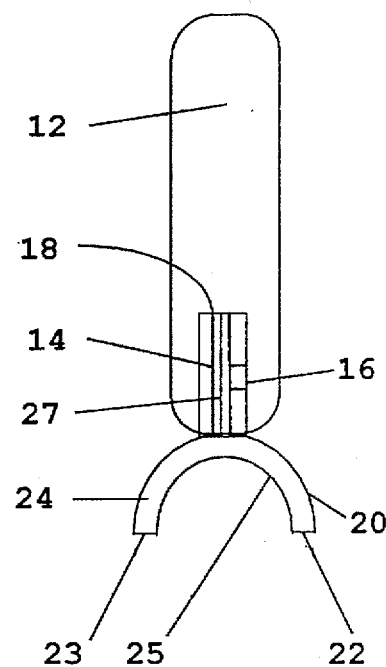
FIG. 2    10

KNIFE FOR LAPAROSCOPIC SURGERY

BACKGROUND OF THE INVENTION

1. Field of the Invention

This invention relates to knives used in enlarging the incision used in laparoscopic surgery.

2. Description of Related Art

The major disorder associated with the gallbladder is the presence of gallstones. The usual treatment for gallstones is surgical removal.

Endoscopic or laparoscopic devices enable surgeons to perform various surgical procedures within body cavities under endoscopic observation and without requiring large surgical incisions. Such procedures are typically done by inserting an endoscope and necessary instruments through one or more openings or incisions of 1 cm or less in length which penetrate a body wall. The process of removing a gall bladder, referred to as a laparoscopic cholecystectomy, begins with the insertion of a hollow needle into the abdominal cavity. A gas, such as carbon dioxide, is injected to create a work place in the abdominal cavity. A trocar having an outer cannula and an inner blade is used to penetrate the abdominal wall and enter the abdominal cavity. The inserted cannula is sometimes referred to as a trocar port.

The inner blade of the trocar is withdrawn leaving the cannula through which various instruments are inserted for the manipulation and detachment of the gall bladder. The gall bladder is drawn to the cannula and withdrawn from the abdominal cavity through the cannula. It is desirable to withdraw the intact gall bladder. This is accomplished by drawing the intact, detached gall bladder to the inner opening of the cannula and then withdrawing the cannula and attached gall bladder from the incision in the abdominal wall. In some cases, however, the diameter of the cannula and of the incision is too small for the gall bladder with the gall stones to traverse the abdominal wall. Such an oversized gall bladder may rupture or be broken by the surgeon, necessitating the laborious and time consuming removal of gall bladder stones from the abdominal cavity.

The incision knife of the present invention is used to enlarge the incision when an oversized gall bladder with stones presents. This incision knife is guided by the cannula by a hemispheric guide which also serves as a shield which prevents inadvertent damage to the gall bladder. The enlarged incision allows the desirable removal of an intact gall bladder, despite its large stones.

Use of an ordinary surgeon's knife or scalpel to enlarge an endoscopic incision is not acceptable because of the hazard of making an incision of uncontrolled length and of the hazard of damaging the gall bladder.

U.S. Pat. No. 5,263,937 discloses a safety trocar which requires reduced force to penetrate the abdominal wall. The trocar has a blade with a shoulder and a shaft. The shaft is inserted in a cannula which approximates the diameter of the shoulder and finger-like segments which smooth the transition between blade and cannula and reduce the force required to penetrate the abdominal wall.

U.S. Pat. No. 5,273,024 discloses instruments for endoscopic surgical procedures for treatment of transverse carpal ligaments. A cannula having a longitudinal groove is used to penetrate the carpal tunnel. A knife is then inserted into and oriented by the groove and used to cut the ligament.

SU 1181640 discloses a medical gouge with a handle, grip, blade, screws, gutter, and bar. The gutter has a curved surface encompassing approximately ¼ of a circle and is attached approximately at a right angle to the blade. The edges of the gutter are sharp-pointed. The gouge is used for multi-plane osteotomy of the body of the os ilium.

None of the prior art knives achieve the purpose of the present invention, that of enlarging a laparoscopic incision allowing the passage of an intact gall bladder.

SUMMARY OF THE INVENTION

The knife of the present invention comprises a handle, a blade attached to the handle, and a hemispheric guide attached at right angles to the handle. The end of the guide extends beyond the blade and acts to protect internal organs from the blade.

In use, the diseased gall bladder is detached and brought to the cannula by standard procedures. If the diseased gall bladder and stones is too large to by withdrawn through the cannula, the knife is used to enlarge the incision, thereby allowing the cannula and attached gall bladder to be withdrawn from the abdominal cavity. The gall bladder then is detached from the cannula and the cannula may be reinserted for final inspection and clean-up of the abdominal cavity. A split stopper is used to fill the space between the cannula and now enlarged incision, thereby allowing reinjection of a gas and re-inflation of the abdominal cavity.

An objective of this invention is to provide a knife which enlarges the incision made in a endoscopic procedure.

A further objective is to provide a knife which enlarges the incision in a laparoscopic cholecystectomy.

A further objective is to provide a knife which enlarges the incision in an endoscopic procedure in a controlled fashion.

A further objective is to provide a knife which is guided by a cannula or trocar in enlarging an incision.

A further objective is to provide a knife having a protective edge which protect internal organs from damage while enlarging an incision.

A further objective is to provide a knife for enlarging a laparoscopic incision which is effective, inexpensive, and reliable.

BRIEF DESCRIPTION OF THE DRAWINGS

FIG. 1 is a side view of the incision knife.

FIG. 2 is a front view of the incision knife.

DESCRIPTION OF THE PREFERRED EMBODIMENTS

Figure 3:
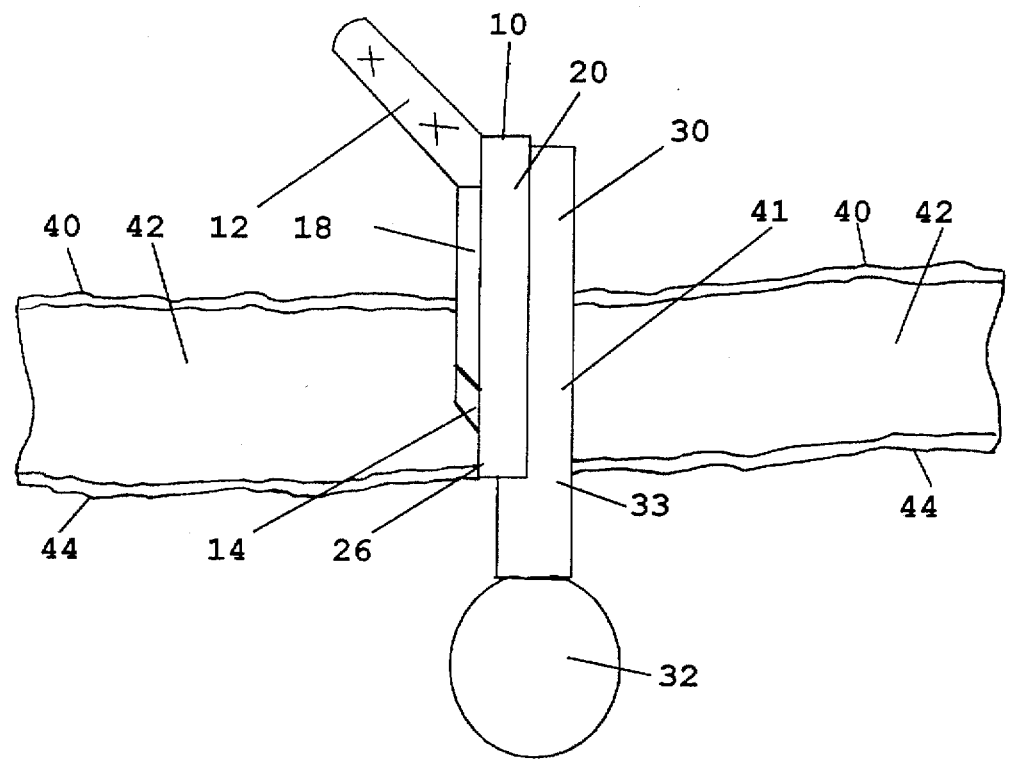
FIG. 3 is a side view of the incision knife in use in enlarging a endoscopic incision during a laparoscopic cholecystectomy.

FIG. 1 is a side view of the incision knife 10. The knife has a handle 12 at the rear end 19 and a ward 26 at the front end 17.

A rectangular wing 18 has long edges 13 and 28 and short edges 11 and 15. A handle 12 is attached to short edge 11 of wing 18. A guide 20 in the form of an elongated hemisphere is attached to long edge 28 of wing 18 with wing oriented along a tangent to the guide 20.

A blade 14 is attached to short edge 15 of wing 18 with the edge 27 of blade 14 exposed toward the front end 17 of knife. Blade 14 is secured to wing 18 by stud 16. Blade 14 is attached to wing 18 at an angle of approximately 45° to the long edge 18 of wing 18.

The rear edge 21, side edges 22 and 23 (shown in FIG. 2), and front edge 24 of guide 20 are rounded. A ward 26, extending beyond blade 14, is formed by the front end of the guide 20.

FIG. 2 is a view of knife 10 from the front end. Handle 12 at the rear end 19 is shown. Guide 20 has rounded side edges 22 and 23, and rounded front edge 24. The inner surface 25 of guide 20 is visible. In use, the inner surface 25 is in contact with the outer surface of a cannula 33 (See FIGS. 3 and 4).

Wing 18 is visible attached to guide 20 along a tangent to guide 20. Blade 14 is attached by stud 16 to wing 18. Blade edge 27 is visible at the front of the knife.

The primary function of curved guide 20 is to guide the knife along a cannula. The curved guide engulfs the outer surface of the cannula and is in contact with and engages the outer surface of the cannula over a substantial portion of the inner surface 25 of curved guide 20. In this example guide 20 is in the form of a hemisphere having 11 mm diameter. This knife is used in conjunction with a cannula having a outer diameter of 10 mm. In this example use of the knife enlarges the incision by approximately 5 mm. The knife may be used repeatedly to provide additional enlargement of the incision.

Guide 20 may have a cross-sectional shape other than hemispheric. It will be readily understood that guide 20 may have an inverted V- or channel-shaped cross-section, or any other shape which will allow contact sufficient between the inner surface of the guide and the outer surface of the cannula to guide and support the knife in enlarging the incision.

The edges 21, 22, 23, and 24 of the guide are rounded, used here to indicate the edges are not sharp. It is necessary only that edge 24 be rounded to protect the gall bladder. Edges 21, 22, and 23 are rounded only for improved appearance and to protect the gloves and hands of the surgeon from accidental injury.

The handle, wing, and blade of the knife may be constructed of any suitable stable, strong, resilient, nontoxic material which may be sterilized, such as steel or plastic or hard rubber. The knife may be reusable or may be constructed of disposable materials for a single use. Plastic is a preferred material of construction.

Blade 14 in this example is a stainless steel No. 11 blade, which is preferred.

FIG. 3 is a side view showing the use of the knife 10 to enlarge the incision 41 made during a laparoscopic cholecystectomy procedure. In the procedure shown in FIG. 3, the cannula 30 is shown after penetration of the abdominal wall 42. A detached gall bladder 32 is shown grasped at the internal end of the cannula 30 by instruments (not shown). The skin 40 is on the external side of the abdominal wall 42 and the inner surface of the abdominal wall is shown at 44. In FIG. 3 the guide 20 is engaged against the outer surface 33 of cannula 30. The surgeon then simply inserts the knife into the abdominal cavity and withdraws it. This procedure enlarges the incision sufficiently to allow withdrawal of the cannula and attached gall bladder through the now enlarged incision. Also visible are the ward 26, the blade 14, wing 18, and handle 12.

In FIG. 3, the knife is shown after having enlarged the incision through about 75% of the thickness of the abdominal wall.

Figure 4:
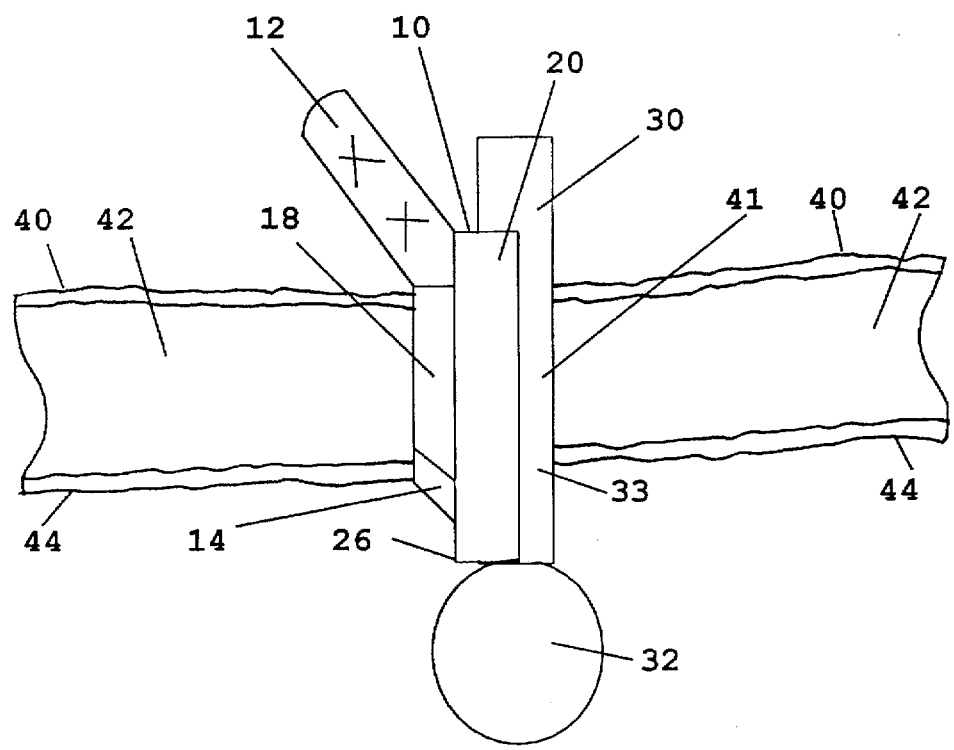
FIG. 4 is a side view of the incision knife in use after the incision enlargement is complete showing the function of the ward in protecting the gall bladder during a laparoscopic cholecystectomy.

In FIG. 4 the knife is shown after enlargement of the incision through the entire thickness of the abdominal wall. The elements are as in FIG. 3. In FIG. 4 the ward 26 is in contact with the gall bladder 32 and protects the gall bladder from injury by the blade 14.

Figure 5:
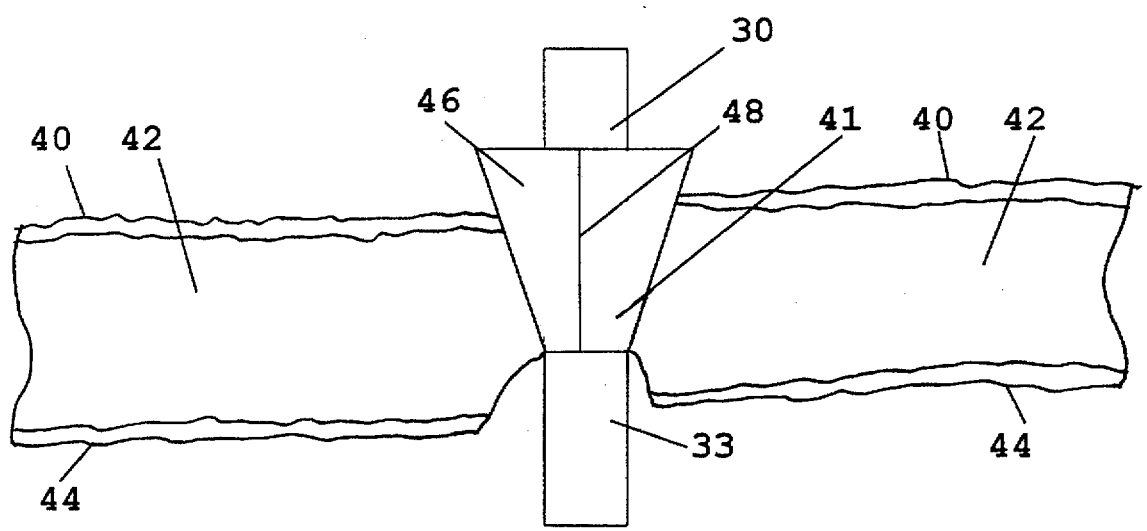
FIG. 5 is a split hollow stopper to center the cannula in an enlarged incision.

FIG. 5 shows the use of a split hollow stopper 46 to center the cannula in an enlarged incision and to seal the enlarged incision so a gas may be injected to inflate the abdomen. The elements of FIG. 5 are as in FIG. 3. A split stopper 46 having a cut 48 along one side is shown in FIG. 5. The stopper 46 extends around the outer surface 33 of the cannula 30 and effectively seals the enlarged incision and prevents the escape of injected gas.

The use of a split stopper allows the stopper to be placed on the cannula without removal of the cannula from the incision. Alternatively, a intact hollow stopper may be used. In this case the stopper must be inserted over one end of the cannula before insertion of the cannula into the incision.

The stopper may be made of any suitable resilient, flexible, sterilizable material. Silicon rubber is a preferred material of construction.

It will be apparent to those skilled in the art that the examples and embodiments described herein are by way of illustration and not of limitation, and that other examples may be used without departing from the spirit and scope of the present invention, as set forth in the appended claims.

I claim:

1. An incision knife for enlarging an incision into which a cannula has been inserted comprising:

a handle, a rectangular wing having a first and a second long edges and a first and a second short edge, said wing attached at said first short edge to said handle, a blade, said blade attached to said wing at said second short edge, a guide for orienting said knife along a cannula with said guide in contact with at least a portion of the outer surface of said cannula, said guide attached to said first long edge of said wing along a tangent to said guide, and said guide having a ward which extends beyond said blade to protect an internal organ from said blade.

2. The incision knife of claim 1 wherein said blade is attached at an angle of approximately 45° to said first long edge of said wing.

3. The incision knife of claim 1 wherein said guide is curved.

4. The incision knife of claim 3 wherein said guide is a hemisphere.

5. The incision knife of claim 1 wherein said guide is V-shaped or channel-shaped.

6. The incision knife of claim 1 wherein said guide has rounded edges.

* * * * *